US009399219B2

(12) United States Patent
Spangler

(10) Patent No.: US 9,399,219 B2
(45) Date of Patent: Jul. 26, 2016

(54) THERMAL ARRAY

(76) Inventor: Frank Leo Spangler, Saint George, UT (US)

( * ) Notice: Subject to any disclaimer, the term of this patent is extended or adjusted under 35 U.S.C. 154(b) by 962 days.

(21) Appl. No.: 12/697,184

(22) Filed: Jan. 29, 2010

(65) Prior Publication Data

US 2010/0210006 A1 Aug. 19, 2010

Related U.S. Application Data

(60) Provisional application No. 61/152,546, filed on Feb. 13, 2009.

(51) Int. Cl.

*C12M 1/34* (2006.01)
*B01L 7/00* (2006.01)

(52) U.S. Cl.

CPC ....... *B01L 7/5255* (2013.01); *B01L 2300/0809* (2013.01); *B01L 2300/1805* (2013.01); *B01L 2300/1822* (2013.01); *B01L 2300/1827* (2013.01); *B01L 2300/1883* (2013.01)

(58) Field of Classification Search

CPC .......... B01L 7/5255; B01L 2300/1805; B01L 2300/1822; B01L 2300/1827; B01L 2300/1883; H05B 3/68; H05B 3/70; H01L 35/34; H01L 21/67103

USPC .................................... 435/287.3, 303.1, 809

See application file for complete search history.

(56) References Cited

U.S. PATENT DOCUMENTS

| | | | | |
|---|---|---|---|---|
| 4,683,202 | A | 7/1987 | Mullis | |
| 4,740,664 | A * | 4/1988 | Payne | G05D 23/24 219/448.12 |
| 4,810,857 | A * | 3/1989 | Goessler | H05B 3/746 219/448.19 |
| 5,455,175 | A | 10/1995 | Wittwer et al. | |
| 5,552,580 | A * | 9/1996 | Pfost et al. | 219/521 |
| 6,767,512 | B1 * | 7/2004 | Lurz et al. | 422/552 |
| 6,821,771 | B2 * | 11/2004 | Festoc | 435/287.2 |
| 7,133,726 | B1 | 11/2006 | Atwood et al. | |

FOREIGN PATENT DOCUMENTS

DE 2335257 A1 * 1/1975 .............. F24C 15/10

OTHER PUBLICATIONS

English language machine translation of DE 2335257A1 (Jan. 1975), pp. 1-2.*

* cited by examiner

*Primary Examiner* — William H Beisner

(74) *Attorney, Agent, or Firm* — Gurr & Brande, PLLC; Robert A. Gurr

(57) ABSTRACT

Traditional thermocyclers are heating devices that change sample temperatures by adding heat energy into a sample block that is usually a large metal block and then extracting that heat energy out of the block in a process called ramping the temperature. Presented herein is a technology that eliminates the large mass sample block and ramping temperatures in a sample block and thus in a sample vessel. This design called a Thermal Array requires a fraction of the energy used to process a sample. In addition, the array allows a much smaller thermal cycler to be designed leading to portability of a device. This technology is designed to allow optimal polymerase chain reactions to be executed.

2 Claims, 6 Drawing Sheets

Top View:

Functional View:

Top View:

Side View:

Functional View:

Circular Array View:

THERMAL ARRAY

CROSS-REFERENCE TO RELATED APPLICATIONS

This application claims priority to U.S. Provisional Application No. 61/152,546, filed on Feb. 13, 2009 by Frank Leo Spangler and entitled "Thermal Array", which is incorporated herein by reference.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The present invention is in the technical field of biotechnology. More particularly, the present invention is in the technical field of polymerase chain reaction (PCR) devices. More particularly, the present invention is in the technical field of portable PCR devices.

Since its invention, the polymerase chain reaction (U.S. Pat. No. 4,683,202) has become a powerful force in biotechnology. It is a method to exponentially amplify essentially exact copes of a DNA segment. DNA is a double stranded molecule and when heated at temperatures such as 95° C., will dissociate into two separate strands. Using small synthetic DNA fragments called primers that can complementary base pair to the dissociated DNA strands at temperatures such as 45-65° C. the primers anneal to the template DNA. Finally, elongation takes place at around 72° C. using an enzyme called a DNA polymerase to extend off of one end of the primer by adding nucleotides (dNTP's) making a new copy strand of DNA. Both of the two DNA strands are used with the annealed primers to make two new copy strands of DNA and these are called elongation events. By repeating the cycle of dissociating, annealing and elongating the reaction again, there is a doubling of new DNA strands produced. Repeat the cycle over 30 times and theoretically there are billions of exact DNA copies in the reaction vessel. These heating and cooling cycles along with the template DNA, primers, dNTP's and DNA polymerase are what constitute the PCR method. PCR is usually performed in automated devices that thermocycle the temperatures needed for the production of amplification products after all of the template DNA, primers, dNTP's and enzyme have been added to a sample vessel.

Conventional PCR devices, such as Peltier thermoelectric devices like the AB 7900 (U.S. Pat. No. 7,133,726 B1), convection heat exchangers like the Roche LightCycler (Wittwer, C. T., et al., Anal. Biochem. 186: p 328-331 (1990) and U.S. Pat. No. 5,455,175) and the like, are typically power hungry and/or difficult to transport. All these PCR devices must thermal cycle in order to heat and cool the samples vessels they hold. The 7900 does this by constructing its sample holder out of a big block of metal and pumping heat energy into and out of the system through thermal conduction. Electrical energy is required both to add heat energy to the sample block and to remove heat energy from the block. This requires a lot of electrical energy due to the large mass of the sample block. The LightCycler avoids the large sample block by using thin capillary tubes with relatively small masses and cycles the temperature by convection with heated air. Like the 7900, the heating element in the LightCycler uses a lot of electrical energy.

Most of these devices are designed to be setup in a laboratory environment and not moved from location to location because they are large and heavy. Moving such devices typically requires a strong person, or a sturdy wheeled vehicle such as a reinforced wagon or handcart. Further, it is common that these devices run off standard 120V outlet for power. Further, the devices cannot readily be moved from room to room once inside a laboratory.

BRIEF SUMMARY OF THE INVENTION

The present invention is a low energy, high efficiency thermal array consisting of a series of heater element, cooling block and heater element placed in tandem. This thermal array vastly reduces to completely eliminates the mass of the sample block while maintaining the higher efficiency of heat transfer by conduction versus convection. The array is in direct contact with the sample vessel throughout the process. This allows for greater control over thermal profile variations. Rather than converting electrical energy to heat energy and adding heat energy to the device and then transferring this energy to a sample block and finally to a sample vessel, the thermal array moves the sample vessel from one heater element to another heater element without ramping the device from one temperature to another. The thermal array converts electrical energy into heat energy, and transfers it directly into the sample vessel. It is more efficient to bring each heater element to temperature and hold them at a target temperature than it is to continually raise and lower the temperature of a heater element in a process called ramping the temperature used by more traditional PCR devices. Because going from one temperature in a sample vessel to another temperature using the thermal array requires only a fraction of a second as the sample vessel is moved from one heater element to the next, thermal cycling of a sample vessel is extremely rapid. Traditional PCR devices have ramp rates of 1.0-2.5° C./sec. and rapid PCR devices have ramp rates of about 5.0° C./sec. Going from 60.0° C. to 95.0° C. could take anywhere from 7.0 to 35.0 seconds in a traditional PCR device while taking less than 0.5 seconds using a thermal array.

DETAILED DESCRIPTION OF THE INVENTION

Figure 1:
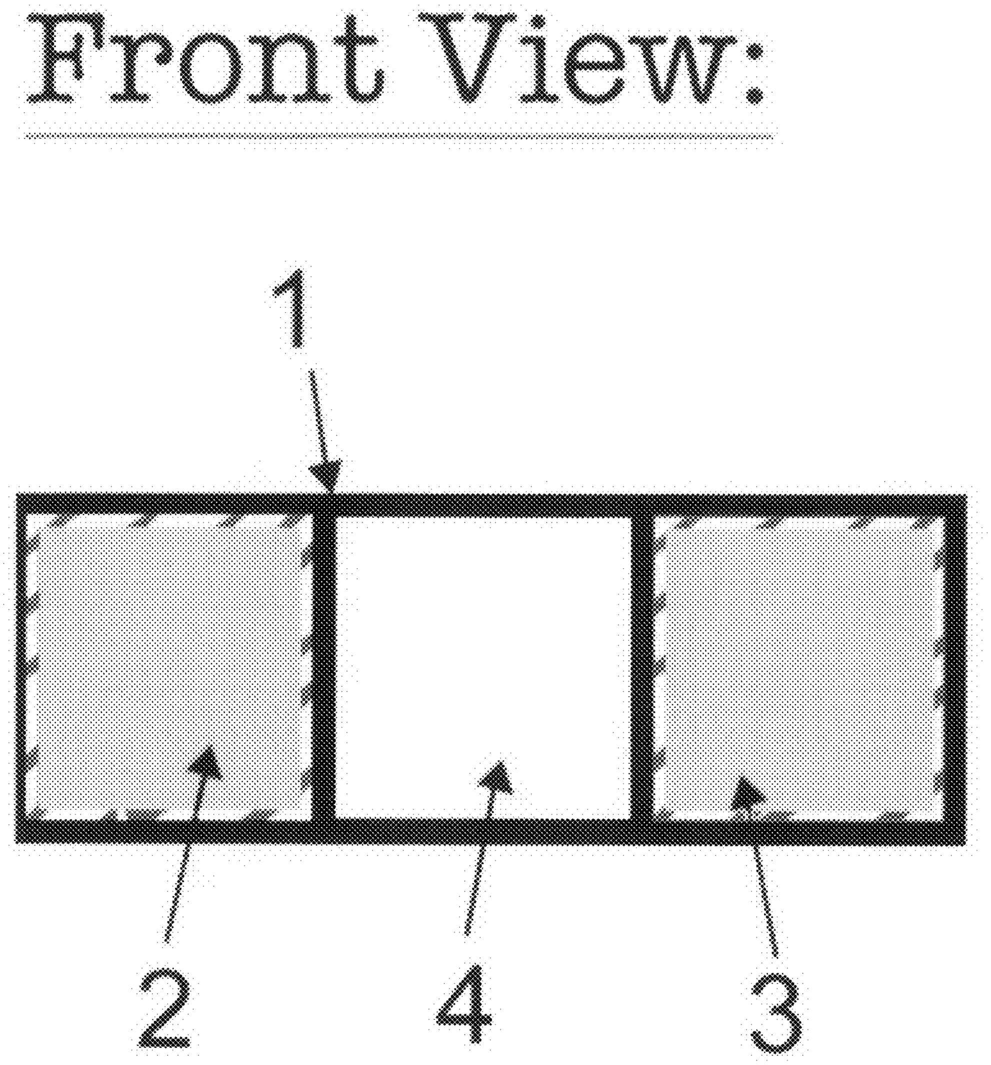
FIG. 1 is a perspective view of a thermal array device in tandem orientation of the present invention.
Figure 2:
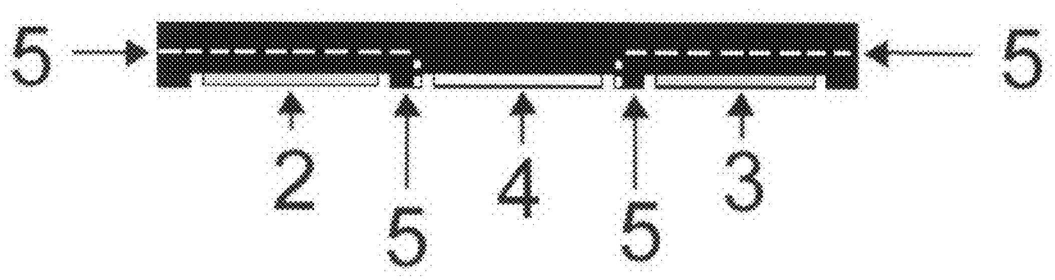
FIG. 2 is a top view of a thermal array device of FIG. 1.
Figure 3:
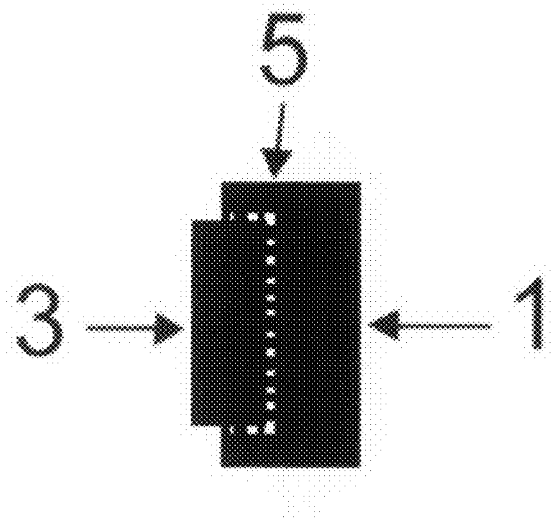
FIG. 3 is a side view of a thermal array of FIG. 1.

Referring now to the invention in more detail, in FIG. 1, FIG. 2 and FIG. 3 there is shown a thermal array 1 having a heating element 2 and a separate heating element 3 held in position by the entire cooling block 4. Each of the heating elements 2 & 3 are attached to the cooling block with insulation 5 covering all four sides and the back of the heating elements. Only the front side of the heating elements 2 & 3 are exposed to conduct heat to a sample vial forming a contact face.

In further detail, still referring to the invention of FIG. 1, FIG. 2 and FIG. 3, the cooling block 4 front portion and the heating elements 2 & 3 front portions are sufficiently wide and long for a sample reaction vessel, such as about 0.5 to 2.0 centimeters long and about 0.5 to about 2.0 centimeters wide. The actual length and width are determined by the size of the reaction vessel. The amount of insulation is large enough to thermally isolate the heating elements 2 & 3 from the cooling block 4.

The construction details of the invention as shown in FIG. 1, FIG. 2 and FIG. 3 are that the array 1 may be made of aluminum or of any other sufficiently rigid and strong material such as high-strength plastic, metal, and the like that also allows for high efficiency thermal conductivity. The insulation material allows the heating elements to be thermally isolated from the cooling block while still in physical contact with it. Further, the various components of the array 1 can be made of different materials.

Figure 4:
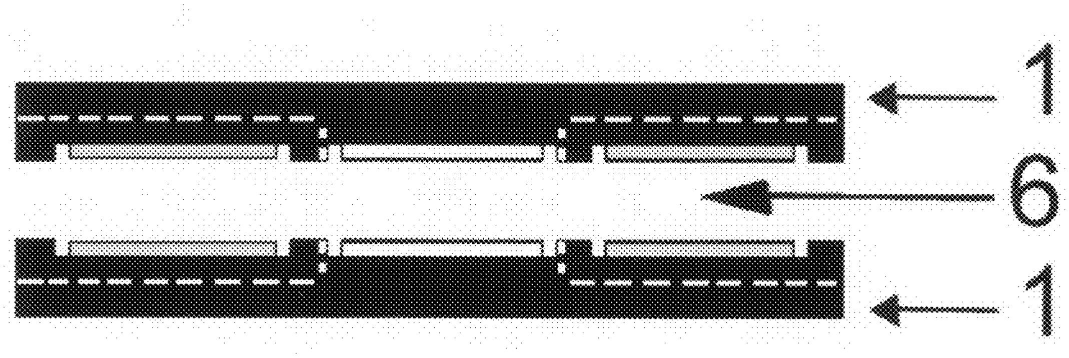
FIG. 4 is a functional view of two arrays making a working PCR device.

Referring now to FIG. 4, there is shown a thermal array 1 positioned directly across from another thermal array 1. These two arrays form a sample channel 6 of a working PCR device.

Figure 6:
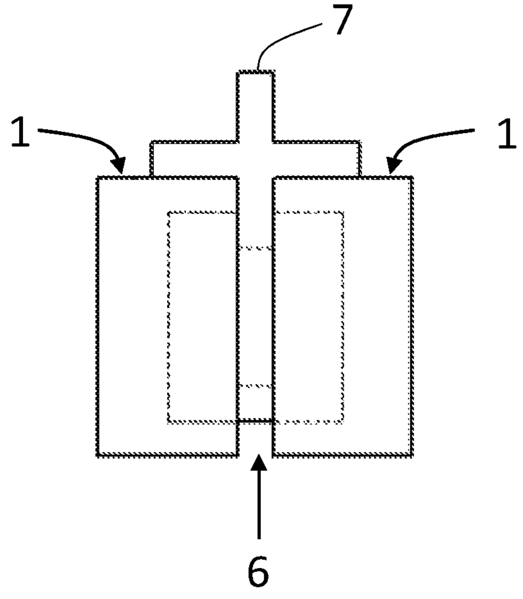
FIG. 6 illustrates two thermal arrays opposite each other with a reaction vessel in a sample channel.

In more detail, referring to the invention of FIG. 4 and FIG. 6, the thermal arrays 1 & 1 as shown form a sample channel 6 where a reaction vessel 7 is placed between the two arrays 1 & 1. A reaction vessel 7 is moved from a heating element to the cooling block to the other heating element and then back to the first heating element or cooling block as reaction requirements dictate.

In further detail, still referring to the invention of FIG. 4, the width of channel 6 is sufficiently wide to accommodate a sample vessel and about 0.05 to about 2.0 centimeters wide but is not limited to these lengths.

Figure 5:
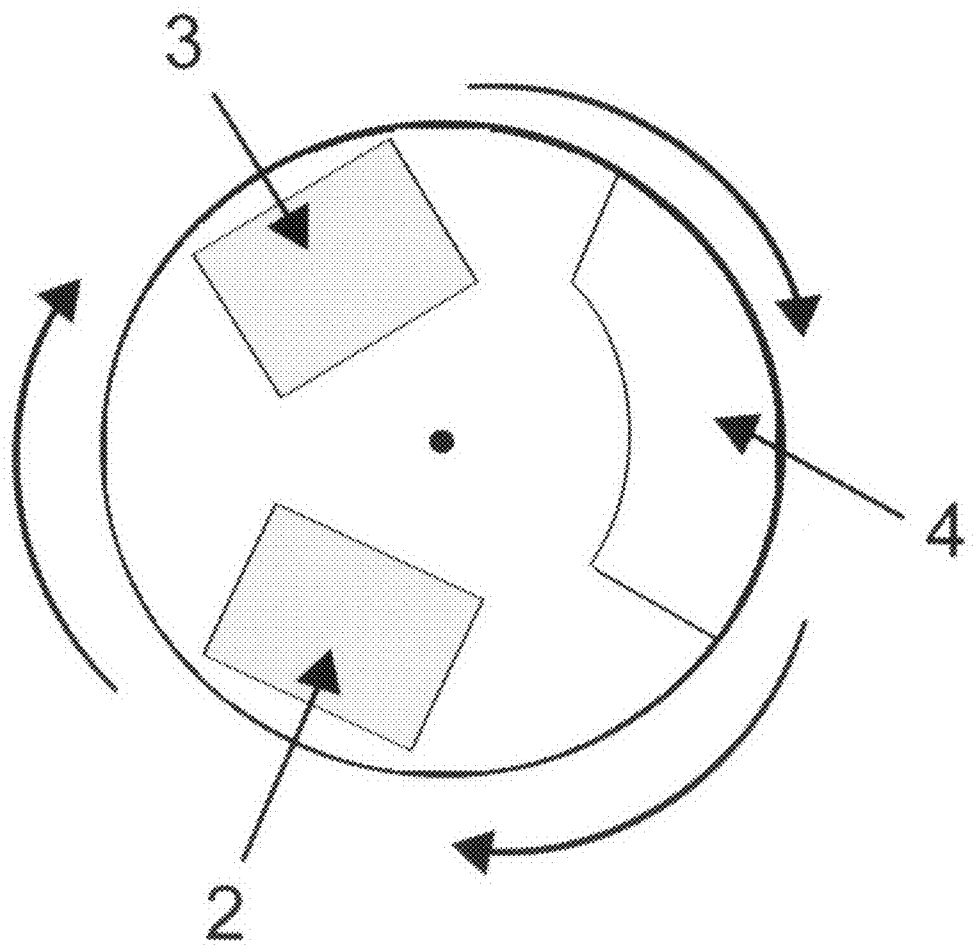
FIG. 5 is a perspective view of a thermal array device in circular orientation of the present invention.

Referring now to FIG. 5, there is shown a thermal array having circular orientation. The circular array has a heating element 2, a cooling block 4 and another heating element 3. The circular array rotates around the axis while a sample reaction vessel remains stationary In further detail, still referring to the invention of FIG. 5, the circular array requires a second circular array to form a working PCR device with a sample channel.

The construction details of the invention as shown in FIG. 5 are that the circular array may be made of aluminum or of any other sufficiently rigid and strong material such as high-strength plastic, metal, and the like that also allows for high efficiency thermal conductivity. The insulation material allows the heating elements to be thermally isolated from the cooling block while still in physical contact with it. Further, the various components of the array 1 can be made of different materials.

Traditional PCR devices change the temperature of a sample vessel by converting electrical energy into heat energy, transferring the heat energy to the device and finally transferring the heat energy to a sample vessel by conduction, convection or radiation. Most of the power budget consumed in traditional devices is ramping from one temperature to another temperature. Maintaining a heater element at a target temperature requires a fraction of the amount of electrical energy that is spent ramping the element to that temperature. Generally speaking the faster the temperature ramp rate the more electrical energy required to reach the target temperature. All of the electrical energy used to transition from one temperature to another is lost to the system because little to no biological activity is taking place in a sample vessel during thermal ramping. A thermal array does not waste any electrical energy ramping the device from one temperature to another. It has distinct temperature elements and moves the sample vessel between them. Essentially all of the heat energy produced by the array is transferred directly into a sample vessel greatly reducing the power budget of a thermal array.

The advantages of the present invention include, without limitation, that it is portable and exceedingly easy to transport. It is easy to move these devices into and around a laboratory or medical office because they are relatively small and lightweight. Moving such a device typically requires a single person. Further, because of the greater efficiency of a thermal array, the devices can be run off batteries. Further, the devices can easily be moved out into the field to locations where services are needed sometimes called point-of-care (POC) or point-of-service (POS).

The cooling block can be either passive or made active by chilling this section of the array with various refrigeration technologies such as, by way of example only, a Peltier element. The junctions between each block are thermally insulated from the other. Small masses can be added to the faces of the heater elements to help stabilize temperature fluctuations. Additional heating elements or cooling blocks may be added to the array as needed. The array allows sample temperature changes to take place in a fraction of a second thus decreasing overall reaction run times.

In broad embodiment, the present invention is a thermal array capable of heating and cooling a sample without changing the temperature of the device elements. This allows the device to be low energy, high efficiency and very portable. It is capable of running on batteries for days to weeks at a time. Other attempts at making a portable PCR device have concentrated on shrinking traditional PCR device technologies into a smaller package. By fundamentally changing how the sample is processed, the thermal array allows heretofore unseen achievements in portability and power budget efficiencies.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

The invention claimed is:

1. A portable thermal-cycling device, comprising:

a first heating element surrounded by insulation on five sides and embedded in a cooling block;

a second heating element surrounded by insulation on five sides and embedded in the cooling block; and wherein the first and second heating elements are separated by a portion of the cooling block, wherein the cooling block comprises at least one Peltier element.

2. A portable thermal-cycling device, comprising:

two arrays opposite each other and forming a sample channel, each array comprising two or more heating elements surrounded by insulation on five sides and embedded in a cooling block; and a reaction vessel within the sample channel.

* * * * *